United States Patent

Melillo et al.

[11] 4,269,772
[45] May 26, 1981

[54] SYNTHESIS OF THIENAMYCIN VIA TRANS-3-CARBOXYMETHYLENE-4-CARBOXY-5-METHYL-$\Delta^2$-ISOXAZOLINE

[75] Inventors: David G. Melillo, Scotch Plains; Kenneth M. Ryan, Clark, both of N.J.

[73] Assignee: Merck & Co., Inc., Rahway, N.J.

[21] Appl. No.: 112,057

[22] Filed: Jan. 14, 1980

[51] Int. Cl.$^3$ .............................................. G07D 487/04
[52] U.S. Cl. ........................ 260/245.2 T; 260/239 A; 260/343.5; 548/240; 560/170
[58] Field of Search ................................... 260/245.2 T Primary Examiner—Mary C. Lee Attorney, Agent, or Firm—James A. Arno; Hesna J. Pfeiffer

[57] ABSTRACT

Disclosed is a process for the stereocontrolled total synthesis of thienamycin, which synthesis proceeds via intermediate II:

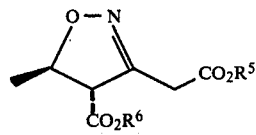

wherein $R^5$ and $R^6$ are removable protecting groups.

1 Claim, No Drawings

SYNTHESIS OF THIENAMYCIN VIA TRANS-3-CARBOXYMETHYLENE-4-CARBOXY-5-METHYL-Δ²-ISOXAZOLINE

BACKGROUND OF THE INVENTION

This invention relates to a stereocontrolled total synthesis of the known antibiotic thienamycin (I).

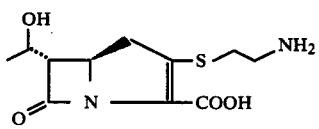

The synthesis proceeds in a stereo-selective way via intermediate II:

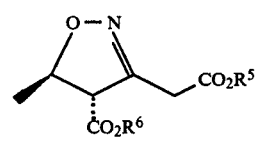

wherein $R^5$ and $R^6$ are removable carboxyl protecting groups such as substituted and unsubstituted: lower alkyl, aryl and aralkyl, such as, for example: methyl; ethyl; t-butyl; 1,1,1-trichloroethyl; benzyl; and phenyl.

DETAILED DESCRIPTION OF THE INVENTION

The process of the present invention may conveniently be summarized by the following reaction diagram:

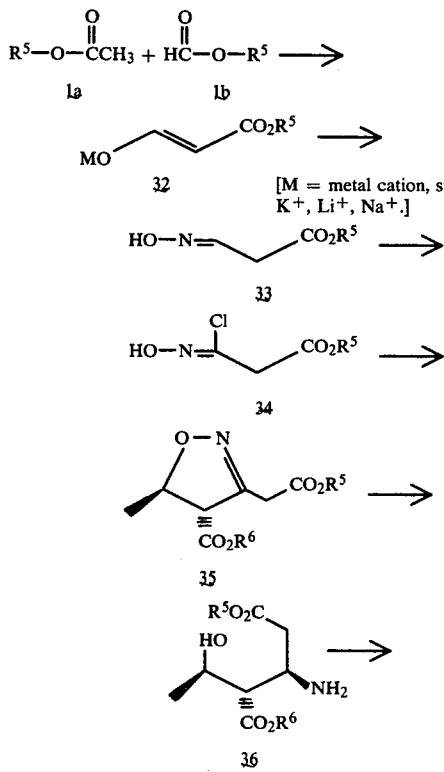

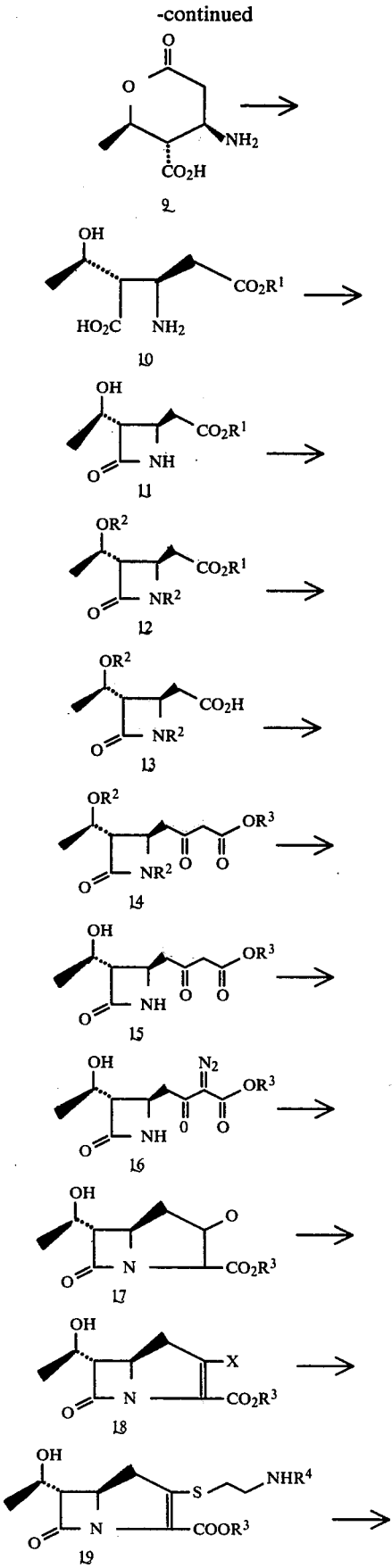

-continued

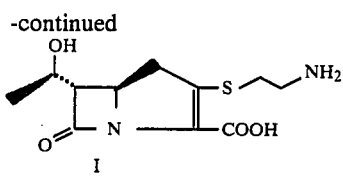

In words relative to the above diagram, equivalent amounts of starting materials 1a and 1b are condensed to form 32. Relative to the known or readily available starting reagents 1a and 1b, $R^5$ is a readily removable carboxyl protecting group which has been identified above. Typically, the reaction is conducted in the presence of an equivalent of a base such as sodium hydride, sodium ethoxide, potassium tert-butoxide or the like in a solvent that preferably allows the precipitation of the enolate 32 as it is formed. Such solvents include ether, toluene or the like. The reaction is typically conducted at a temperature of from 0° to 110° C. for from 0.5 to 24 hours. In the drawing representing the enolate 32, M is a metal cation such as potassium, lithium or sodium, for example, and is derived from the identity of the base reagent.

The transformation 32→33 is conducted by treating the enolate 32 in a solvent such as water, methanol, ethanol, dimethylformamide or the like with an equivalent amount of hydroxylamine, hydrochloride at a temperature of from −10° to 100° C. for from 1 minute to 24 hours.

The transformation 33→44 is accomplished by treating aldoxime 33 in a solvent such as dilute aqueous HCl, methylene chloride, ethyl acetate, diethyl ether, toluene and the like with an equivalent of chlorine gas at from −60° to 25° C. for from 10 minutes to 3 hours.

The transformation 34→35 is accomplished by reacting 34 and a stoichiometric to 20-fold excess of crotonic ester (the value of $R^6$ in structure 35 is determined by the precise identity of the chosen crotonic ester; preferred values for $R^6$ have been described above; a convenient and representative member of this group is $R^6$=methyl) with an equivalent of a base such as pyridine, triethylamine, or the like in a solvent such as toluene, methylene chloride, ethyl acetate, or the like at a temperature of from 0°–100° C. for from 20 minutes to 20 hours.

The reduction 35→36 is accomplished typically by catalytic hydrogenation; for example, 35, in a solvent such as methanol, ethyl acetate, acetic acid, ether, aqueous hydrochloric acid or the like under a hydrogen pressure of from 1–10 atmospheres in the presence of a catalyst such as Raney nickel, palladium on charcoal, platinum oxide or the like is held at a temperature of from 0° to 80° C. for from 1 to 24 hours.

Cyclization of 36 to form the lactone 9 is accomplished by treating 36 in a solvent such as methylene chloride, ether, toluene, water, or the like with an acid such as hydrochloric, sulfuric, phosphoric, trifluoroacetic or the like at a temperature of from 0° to 100° C. for from 0.5 to 20 hours.

The transformation 9→10 is accomplished by treating 9 with an alcohol such as benzyl alcohol, 2,2,2-trichloroethanol, methanol, phenol or the like at a temperature of from 25° to 100° C. for from 1 to 24 hours. The value of $R^1$ is determined by the alcohol $R^1OH$ utilized in the transformation 9→10. Suitable values for $R^1$ additionally include those previously mentioned for $R^5$ and $R^6$.

The transformation 10→11 is accomplished by treating 10 with dicyclohexylcarbodiimide (DCC), or the like in the presence of a base such as triethylamine, 4-dimethylaminopyridine, pyridine, or the like.

Alternatively, intermediate 9 may be converted directly to 11 in a single reaction by treating 9 in a solvent such as acetonitrile, acetone, nitromethane, or the like with the alcohol (benzyl, 2,2,2-trichloroethyl, methyl), the base, such as triethylamine, and the dicyclohexylcarbodiimide at a temperature of from 25° to 100° C. for from 4 to 24 hours.

Establishment of protecting group $R^2$ is accomplished by the transformation 11→12. Preferably 11 in a solvent such as dimethylformamide, ethyl acetate, methylene chloride, or the like is reacted with a reagent capable of establishing $R^2$. Preferred protecting groups are triorganosilyls such as tert-butyldimethylsilyl, or the like. Typically, protecting groups $R^2$ are established by treating 11 in a solvent such as dimethylformamide, ethylacetate, methylene chloride, or the like in the presence of a base such as pyridine, triethylamine, or the like with a stoichiometric to 4-fold excess of tert-butyldimethylsilyl chloride at a temperature of from 25° to 70° C. for from 3 to 48 hours.

It should be noted that establishment of protecting group $R^2$ is optional; the chain elongation reaction 13→14 can advantageously be accomplished when $R^2$=hydrogen.

The deblocking of the carboxyl group is accomplished in the transformation 12→13. Typically, the deprotection is accomplished by catalytic hydrogenation. Typically, 12 and the solvent such as methanol, ethylacetate, ether or the like under a hydrogen pressure of from 1 to 3 atmospheres in the presence of a hydrogenation catalyst such as palladium on charcoal, platinum oxide, or the like is held at a temperature of from 0° to 40° C. for from 1 to 3 hours, to provide 13. Other deblocking procedures, such as hydrolysis, are also appropriate. Thus, for example, when $R^1$ is methyl, basic hydrolysis is preferred: Typically, this is accomplished by the addition of an equivalent amount of a base such as NaOH, KOH, Ba(OH)$_2$, Na$_2$CO$_3$, or the like to an aqueous solution of 12 (for example, as the methyl ester) at 25°–100° C. for from 1.0 min. to 10 hours.

The addition 13→14 is accomplished by treating 13 with 1,1′-carbonyldimidazole or the like in a solvent such as tetrahydrofuran, dimethoxyethane, or the like at a temperature of from 0° to 50° C., followed by the addition of 1.1 to 3.0 equivalents of $(R^3O_2CCH_2CO_2)_2$ Mg or the like at a temperature of from 0° to 50° C. for from 1 to 48 hours. $R^3$ is a readily removable carboxyl protecting groups such as p-nitrobenzyl, o-nitrobenzyl, benzyl and the like.

The removal of the protecting groups $R^2$ is accomplished by treating 14 in a solvent such as 10% aqueous methanol, tetrahydrofuran, or the like in the presence of hydrochloric acid, sulfuric acid, phosphoric acid, or the like at a temperature of 0° to 50° C. for from 10 minutes to 10 hours to provide intermediate 15.

The diazotization reaction 15→16 is accomplished by treating 15 in a solvent such as ethyl acetate, methylene chloride, toluene, or the like, with a diazotization reagent such as p-toluenesulfonyl azide, p-carboxybenzenesulfonyl azide or the like in the presence of a base such as pyridine, triethylamine, or the like at a temperature of from 0° to 40° C. for from 10 to 120 minutes.

Cyclization (16→17) is accomplished by treating 16 in a solvent such as benzene, toluene, THF or the like at a temperature of from 50°–110° C. for from 1–5 hours in the presence of a catalyst such as bis (acetylacetonato) Cu (II) [Cu(acac)$_2$], CuSO$_4$, Cu powder, Rh$_2$(OAc)$_4$, or Pd(OAc)$_2$. Alternatively, the cyclization may be accomplished by irradiating 16 through a pyrex filter (a wave length greater than 300 nm) in a solvent such as benzene, CCl$_4$, diethylether or the like at a temperature of from 0°–25° C. for from 0.5 to 2 hours. ["OAc"=acetate].

Establishment of leaving group X (17→18) is accomplished by reacting the keto ester 17 with R° X such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like; wherein: X is the corresponding leaving group such as toluene sulfonyloxy, p-nitrophenylsulfonyloxy, methanesulfonyloxy, p-bromophenylsulfonyloxy; or other leaving groups which are established by conventional procedures and are well known in the art. Typically, the above reaction to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.5 to 5 hours. The leaving group X of intermediate 18 can also be halogen. The halogen leaving group is established by treating 17 with a halogenating agent such as φ$_3$PCl$_2$, φ$_3$PBr$_2$, (φO)$_3$PBr$_2$, oxalyl chloride or the like in a solvent such as CH$_2$Cl$_2$, CH$_3$CN, THF, or the like in the presence of a base such as diisopropylethylamine, triethylamine, or 4-dimethylaminopyridine or the like. [φ=phenyl.]

The leaving group X can also be a phosphate. It is typically prepared by treating 17 with diethyl chlorophosphate or the like in the presence of a base such as diisopropylethylamine, triethylamine, or 4-dimethylaminopyridine or the like.

The leaving group X can also be a carbonate. It is prepared by treating 17 with a chloroformate such as methyl, benzyl, p-nitrobenzyl or the like in the presence of a base such as diisopropylethylamine, triethylamine, or 4-dimethylaminopyridine or the like.

The leaving group X can also be an imino ester:

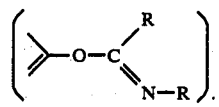

It is prepared by treating 17 with an imidoyl chloride such as N-phenyl trimethylacetamido chloride in the presence of a base such as diisopropylethylamine, triethylamine, or 4-dimethylaminopyridine or the like.

The reaction 18→19 is accomplished by treating 18 in a solvent such as dioxane, dimethylformamide, dimethylsulfoxide, acetonitrile, hexamethylphosphoramide, or the like in the presence of an approximately equivalent to excess of the mercaptan reagent HSCH$_2$CH$_2$NHR$^4$ wherein R$^4$ is hydrogen or a readily removable N-protecting group such as p-nitrobenzyloxycarbonyl, o-nitrobenzyloxycarbonyl, formimidoyl, phenoxyacetyl, phenylacetyl, 2-methyl-2-(o-nitrophenoxy)propionic, and o-nitrophenoxyacetic, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH$_2$CH$_2$NHR$^4$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 19→I is accomplished by conventional procedures such as hydrolysis or hydrogenation, or enzymatically. Typically 20 in a solvent such as dioxane-water-ethanol; tetrahydrofuran-aqueous dipotassium hydrogen phosphate-isopropanol; tetrahydrofuran-water-morpholinopropane-sulfonic acid (adjusted pH to 7.0 by adding sodium hydroxide); or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.5 to 4 hours to provide I.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

(2SR, 3RS)-3-amino-2[1(RS)-hydroxyethyl]-pentanedioic acid 5-benzyl ester hydrochloride

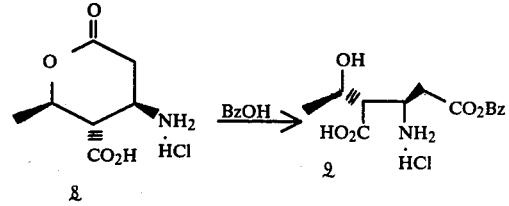

A suspension of the lactone (1.65 g, 0.0079 mmoles) in 10 ml. benzyl alcohol is heated at 70° for 1.5 hrs. The mixture is cooled to room temperature, diluted with 70 ml CH$_3$CN, and aged for 30 minutes. The product is filtered, washed with 3 portions of CH$_3$CN, and dried in vacuo to give the product 2 (2.10 g) as a white powder.

EXAMPLE 2

(3SR, 4RS)-3-[1(RS)-hydroxyethyl]-2-oxo-4-azetidineacetic acid benzyl ester

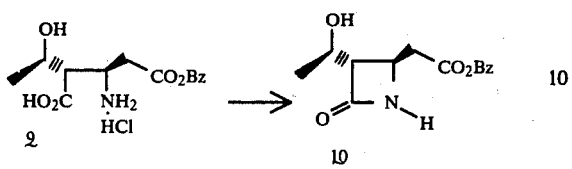

A suspension of the amino acid (2.93 g, 9.22 mmole) in CH₃CN (40 ml) is treated with NEt₃ (0.95 g, 9.14 mmole) followed by N,N'-dicyclohexylcarbodiimide (2.08 g, 10.1 mmole). The resulting suspension is aged at room temperature for 10 min. and then heated to 60° for 5 hrs. The reaction mixture is concentrated, the residue is slurried in EtOAc, and the precipitated urea is removed by filtration. The filtrate is washed successively with 1 N aqueous HCl, saturated aqueous NaHCO₃, H₂O and then dried with MgSO₄ and concentrated to yield 10 as a white solid. An analytical sample is prepared by recrystallization from a hexane-ethyl acetate mixture to give white needles, mp 99°–101.5°.

| Elem. Anal. Calcd. | | Calcd. | Found |
|---|---|---|---|
| for $C_{14}H_{17}NO_4$ | C | 63.86 | 64.05 |
| | H | 6.51 | 6.50 |
| | N | 5.32 | 5.25 |

EXAMPLE 3

(3SR, 4RS)-3-[1(RS)-hydroxyethyl]-2-oxo-4-azetidineacetic acid benzylester 10

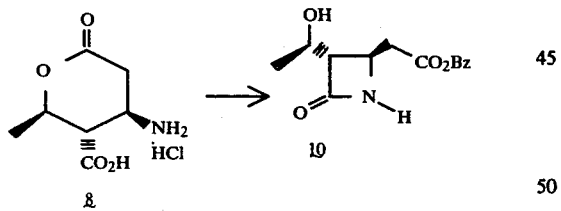

A suspension of the lactone (1.68 g, 8.0 mmole) in 10 ml. benzyl alcohol is heated to 70° for 2 hours. The solution is cooled to room temperature and a solution of NEt₃ (0.97 g, 9.6 mmole) in 10 ml MeCN is added followed by solid N,N'-dicyclohexylcarbodiimide (1.81 g, 8.80 mmole). The suspension is stirred at room temperature for 15 minutes then at 70° for 3.5 hours. The suspension is diluted with EtOAc, cooled to 0°, and filtered. The filtrate is washed successively with H₂O, 1 N aqueous HCl, H₂O, satd. NaHCO₃, H₂O, and then it is dried over MgSO₄ and concentrated in vacuo to an oily solid. The β-lactam is purified by crystallization from hexane/EtOAc or chromatography on silica gel (the product 10 is obtained as a white solid from 75% EtOAc/hexane fractions, 0.90 g).

EXAMPLE 4

(3SR, 4RS)-1-(tert-butyldimethylsilyl)-3-[1(RS)-tert-butyl-dimethylsilyloxyethyl]-2-oxo-4-azetidineacetic acid benzyl ester 11

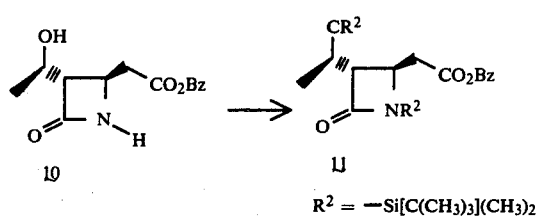

$R^2 = -Si[C(CH_3)_3](CH_3)_2$

Triethylamine (0.937 g, 9.28 mmole) in 3 ml DMF (sieve-dried) is added to the β-lactam (1.056 g, 4.01 mmol) in 15 ml DMF at room temperature. The solution is chilled to 0° and tert-butyldimethylsily chloride (1.39 g, 9.28 mmole) is added as a solid in 3 portions over 5 minutes. The suspension is aged at 0° for 15 minutes then at room temperature for 19 hours. The orange-brown suspension is diluted with H₂O and extracted with EtOAc. The organic layer is washed with H₂O, brine, dried and concentrated to give the product 11 as a colorless gum (2.0 g) that solidifies on standing.

EXAMPLE 5

(3SR, 4RS)-1-(tert-butyldimethylsilyl)-3-[1(RS)-tert-butyl-dimethylsilyloxyethyl]-2-oxo-4-azetidineacetic acid 12

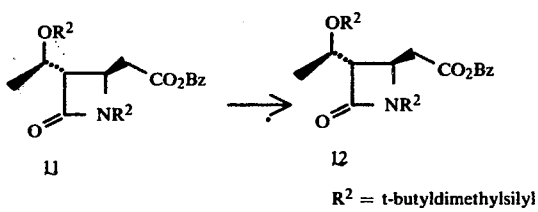

$R^2$ = t-butyldimethylsilyl

A suspension of the crude benzyl ester 11 (2.00 g, 4.01 mmole) and ½ g 10% Pd/C in 40 ml. MeOH is pressurized (40 psi) with H₂ and shaken for 75 minutes. The suspension is filtered and the filtrate is concentrated in vacuo to give the product 12 as a white solid, 1.60 g.

Analytical sample from EtOAc as white needles, m.p. 168°–9°.

| Calcd. for | | Calculated | Found |
|---|---|---|---|
| $C_{19}H_{39}NO_4Si_2$ | C | 56.81 | 56.95 |
| | H | 9.79 | 9.98 |
| | N | 3.49 | 3.45 |
| | Si | 13.98 | did not analyze properly |

EXAMPLE 6

(3SR,4RS)-1-(tert-butyldimethylsilyl)-3-[1(RS)-tert-butyl-dimethylsilyloxyethyl]-β,2-dioxo-4-azetidinebutanoic acid p-nitrobenzyl ester 13

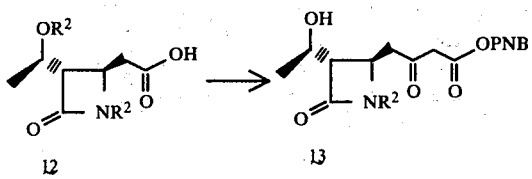

PNB = p-nitrobenzyl
R² = t-butyldimethylsilyl

To a solution of the β-lactam 12 (1.46 g., 3.62 mmole) in 30 ml. CH₂Cl₂ at room temperature is added 1,1'-carbonyldiimidazole (0.64 g., 3.95 mmole). After stirring for 30 minutes the solution is treated with 2,2-dimethyl-1,3-dioxane-4,6-dione (0.78 g., 5.43 mmole) and 4-dimethylaminopyridine (0.66 g., 5.43 mmole) and the solution aged at room temperature for another 70 hours. The solution is washed with 1 N aqueous HCl followed by H₂O and then dried with Na₂SO₄ and concentrated. The residue is dissolved in 20 ml. MeCN, p-nitrobenzyl alcohol (0.94 g., 6.15 mmole) is added, and the solution is heated to reflux for 1 hour. The reaction mixture is concentrated to a gummy solid. The pure product 13 is isolated by crystallization from isopropanol; or by chromatography on silica gel (eluent, hexane-EtOAc, 7/3).

Analytical sample from 1/1 hexane/Et₂O, colorless needles, m.p. 113.5°–115°.

| Calcd. for | | Calcd. | Found |
|---|---|---|---|
| C₂₈H₄₆N₂O₇Si₂ | C | 58.09 | 58.31 |
| | H | 8.01 | 8.25 |
| | N | 4.84 | 4.76 |
| | Si | 9.70 | did not analyze properly |

EXAMPLE 7

(3SR,4RS)-3-(1(RS)-hydroxyethyl)-β,2-dioxo-4-azetidinebutanoic acid p-nitrobenzyl ester

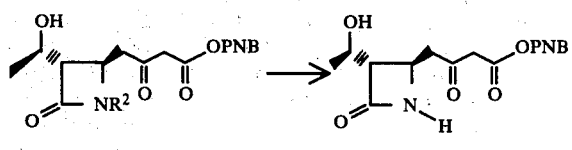

PNB = p-nitrobenzyl
R² = t-butyldimethylsilyl

Concentrated aqueous HCl (0.45 ml) is added to a suspension of the silyl derivative (0.63 g., 1.09 mmole) in 30 ml. of 10% aqueous MeOH. After stirring at room temperature for 6 hours, the solution is concentrated almost to dryness. The residue containing 14 is partitioned between H₂O and CH₂Cl₂. The organic layer is dried (MgSO₄) and concentrated to a colorless gum, 0.40 g. The crude product is used as is in the next step.

Analytical sample from hexane/EtOAc, m.p. 97°–9°.

| Calcd. for | | Calcd. | Found |
|---|---|---|---|
| C₁₆H₁₈N₂O₇ | C | 54.85 | 55.02 |
| | H | 5.18 | 5.38 |
| | N | 8.00 | 7.79 |

EXAMPLE 8

(3SR,4RS)-α-diazo-3-[1(RS)-hydroxyethyl]-β,2-dioxo-4-azetidinebutanoic acid p-nitrobenzyl ester 15

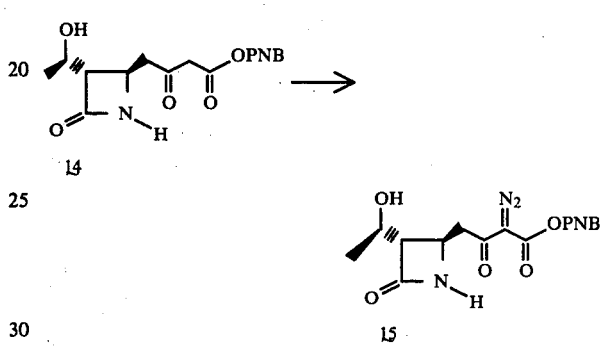

A solution of the crude β-keto ester 14 (0.83 g., 2.37 mmole) and p-toluenesulfonyl azide (0.56 g, 2.85 mmole) in 10 ml EtOAc at room temperature is treated with a solution of NEt₃ (0.31 g., 3.08 mmole) in 2 ml. EtOAc. The resulting suspension is stirred for 1 hr., chilled to 0° and filtered. The product 15 (0.77 g) is analytically pure, m.p. 160.5°–2° (dec.).

| Elem. Anal. | | Calcd. | Found |
|---|---|---|---|
| C₁₆H₁₆N₄O₇ | C | 51.06 | 51.04 |
| | H | 4.29 | 4.22 |
| | N | 14.89 | 14.76 |

EXAMPLE 9

(5RS,6SR)-6-[(RS)-1-hydroxyethyl]-3,7-dioxo-1-azabicyclo[3.2.0]heptane-2-carboxylic acid p-nitrobenzyl ester

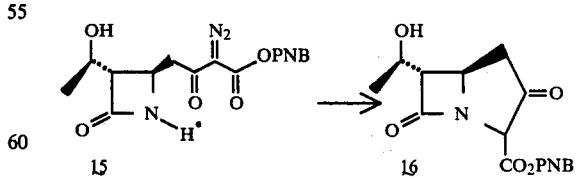

A stirred suspension of the diazo compound 15 (500 mg, 1.33 mmole) and rhodium diacetate (15 mg) in dry toluene (35 ml) is heated to 80°–5° for 2.5 hours. After filtration of the catalyst, the solution is concentrated in vacuo to give the product as a white solid, mp 92°–8°.

EXAMPLE 10

(5RS,6SR)-6-[(RS)-1-hydroxyethyl]-3-[2-(p-nitrobenzyloxycarbonyl)aminoethylthio]-7-oxo-1-azabicyclo[3.2.0]hept-2-ene-2-carboxylic acid p-nitrobenzyl ester

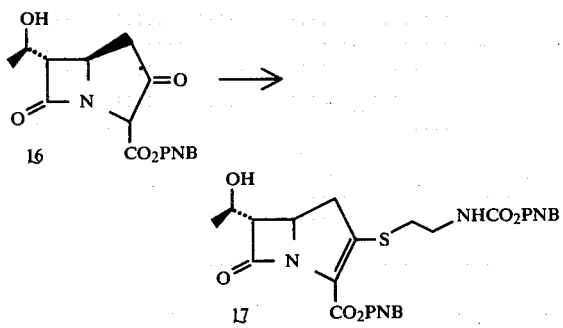

PROCEDURE A: Trifluoromethylsulfonyl Activation

To a stirred suspension of the bicyclic ketone 16 (100 mg, 0.287 mmole) in dry methylene chloride (1 ml) is added dropwise a solution of diisopropylethylamine (62 mg, 0.481 mmole) in dry CH$_2$Cl$_2$ (0.4 ml) at 0° C. under a nitrogen atmosphere. The resulting mixture is aged for 15 min. then trifluoromethanesulfonic anhydride (90 mg, 0.319 mmole) is added to give a clear solution. To the mixture is added a solution of diisopropylethylamine (250 mg, 1.94 mmole) in CH$_2$Cl$_2$ (0.3 ml) followed by N-p-nitrobenzyloxycarbonylcysteamine (77 mg, 0.30 mmole) as a solid at 0° C. The mixture is stirred for 30 min during which time the product crystallizes as a colorless solid. The solid is collected by filtration and washed with CH$_2$Cl$_2$. An additional crop of product is obtained by washing the filtrate with dilute aqueous NaHCO$_3$. The organic layer is dried with Na$_2$SO$_4$ and concentrated in vacuo. The residue is crystallized from EtOAC. The combined yield is 108 mg (64%) of product 17.

PROCEDURE B: Tosylate Activation

To a suspension of the bicyclic ketone 16 (50 mg, 0.144 mmole) in acetonitrile (3 ml) is added dropwise a solution of diisopropylethylamine (22 mg, 0.171 mmole) in 1 ml CH$_3$CN at −5° C. under a nitrogen atmosphere. After aging at this temperature for 10 min, a solution of p-toluene sulfonic anhydride (51 mg, 0.156 mmole) in 1 ml CH$_3$CN is added. The resulting mixture is stirred for 2 hr. at 0° C. The solution is concentrated in vacuo to a volume of approximately 1 ml and then 3 ml of dry N,N-dimethylformamide (DMF) is added and the remaining CH$_3$CN removed in vacuo. To the DMF solution at −5° C. is added a solution of diisopropylethylamine (40 mg, 0.31 mmole) in 0.5 ml DMF and the resulting mixture stored in a refrigerator for 70 hrs. The solution is diluted with brine and extracted with five portions of CH$_2$Cl$_2$. The combined extracts are washed with brine, dried over Na$_4$SO$_4$, and concentrated in vacuo. The residue is crystallized from an ethylacetate-ether mixture to give the product 17 as a colorless solid, 68 mg (81%).

PROCEDURE C: Phosphate activation

To a suspension of the bicyclic ketone 16 (100 mg, 0.29 mmole) in CH$_3$CN (1 ml) is added dropwise a solution of diisopropylethylamine (37 mg, 0.29 mmole) in 0.4 ml CH$_3$CN at 0° under a nitrogen atmosphere. The resulting mixture is stirred for 15 min then a solution of diphenyl chlorophosphate (77 mg, 0.29 mmole) in 0.4 ml CH$_3$CN is added. The mixture is stirred for 15 min at 0° and then 15 min at room temperature. The mixture is again cooled to 0° and a solution of diisopropylethylamine (38.7 mg, 0.30 mmole) in 0.4 ml CH$_3$CN is added followed by N-p-nitrobenzyloxycarbonylcysteamine (77 mg, 0.30 mmole). The reaction mixture is stored overnight in a freezer, diluted with EtOAC, and filtered to give the product 17 as a colorless solid, 118 mg (70%).

EXAMPLE 11

Thienamycin

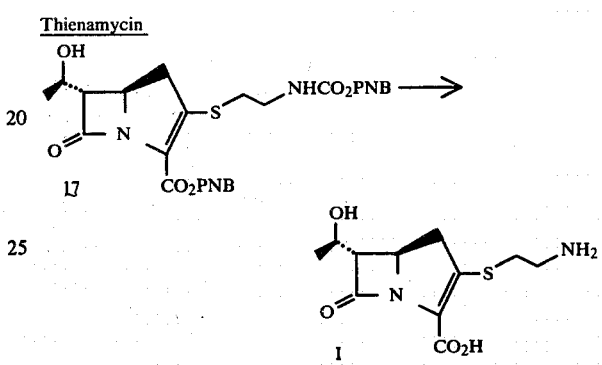

A mixture of the protected thienamycin 17 (4.9 mg, 8.362×10$^{-6}$ mole) and platinum oxide (3.4 mg) in tetrahydrofuran (2 ml), water (1 ml) and 0.5 M morpholinopropane sulfonic acid (adjusted to pH 7.0 by adding sodium hydroxide) (0.5 ml) is hydrogenated at 40 psi on a Parr shaker for 60 minutes. The suspension is filtered to remove catalyst and the catalyst is washed with water (2×20 ml). The filtrate is washed with EtOAC (2×15 ml). The aqueous layer is diluted to 50 ml and assayed for thienamycin.

UV $\lambda_{max}$=298 mm.

HPLC assay 81.4% yield, retention time=298 sec., natural thienamycin 298 sec.

EXAMPLE 12

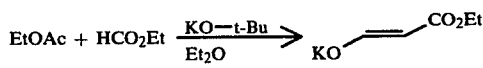

A mixture of ethyl acetate (44 g, 0.5 mole) and ethyl formate (37 g, 0.5 mole) is added dropwise over 1 hour to a cold (−10° C.), stirred suspension of potassium tert-butoxide (56.1 g, 0.5 mole) in 200 ml diethyl ether. The thick suspension is stirred at room temperature for 16 hours, then cooled to 0° and filtered. The collected solid is washed with three portions of ether and dried in vacuo to constant weight (45 g).

EXAMPLE 13

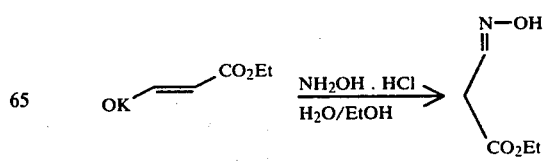

The enolate (4.62 g, 0.03 mol) is added as a solid to a cold (0°) solution of hydroxylamine hydrochloride (2.08 g, 0.03 mol) in 10 ml of water. Ethanol (2 ml) is added, the cooling bath is removed, and the solution is aged for 30 minutes. The solution is extracted with two portions of CHCl₃ and the combined extracts are dried (MgSO₄) and concentrated to give the aldoxime (2.87 g) as a yellow solid. The product is approximately 95% pure and is a mixture of syn- and anti-isomers as determined by NMR spectroscopy.

EXAMPLE 14

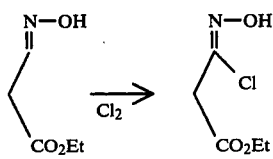

Chlorine gas (4.3 g, 60.6 mmole) is introduced into a cold (−10°) solution of the aldoxime (8.00 g, 61.1 mmole) in 100 ml. of 5% aq. HCl. The solution is aged for 30 min. and then the product is extracted into 3 portions CH₂Cl₂. The extracts are dried (CaCl₂) and concentrated in vacuo to give the chloride as a pale green liquid (8.45 g.).

EXAMPLE 15

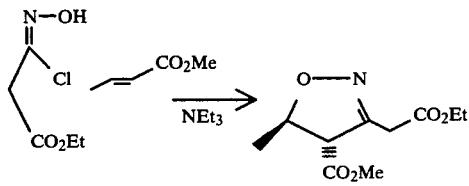

A solution of NEt₃ (5.14 g, 50.9 mmole) in 20 ml toluene is added dropwise over 75 minutes to a stirred solution of the chloride (8.45 g, 50.9 mmole) and methyl crotonate (30.5 g, 305 mmole) in 40 ml toluene. The suspension is aged at room temp. for 2.5 hrs. and then it is washed with two portions of H₂O and concentrated to an orange oil. Chromatography on 250 g silica gel and elution with 6% EtOAc/toluene gives the product as a pale yellow oil (5.92 g).

EXAMPLE 16

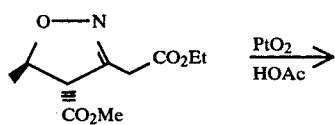

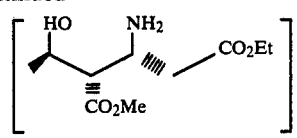

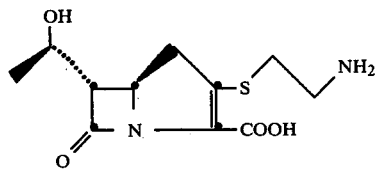

A suspension of the isoxazoline (3.10 g, 13.5 mmole) and PtO₂(800 mg) in HOAc (50 ml) is stirred at room temperature under 40 psi H₂ for 4 days. The suspension is filtered and the solution concentrated in vacuo. The residual gum is dissolved in 50 ml conc. aq. HCl and refluxed for 3 hours and then concentrated. The residue is crystallized from HOAc to give the lactone as a white solid.

CROSS REFERENCE TO RELATED APPLICATIONS

The following concurrently filed, commonly assigned U.S. patent applications are similarly directed to totally synthetic schemes for the preparation of thienamycin and in that respect complement the disclosure of the present application; consequently, these applications are incorporated herein by reference.

1. U.S. patent application Ser. No. 112,058 filed Jan. 14, 1980.
2. U.S. patent application Ser. No. 112,020 filed Jan. 14, 1980.
3. U.S. patent application Ser. No. 112,021 filed Jan. 14, 1980.
4. U.S. patent application Ser. No. 112,035 filed Jan. 14, 1980.
5. U.S. patent application Ser. No. 112,022 filed Jan. 14, 1980.

What is claimed is:
1. A process for preparing:

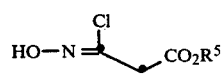

and its pharmaceutically acceptable salts which comprise the cycloaddition of:

with

CH₃CH=CHCOOR⁶ to form:

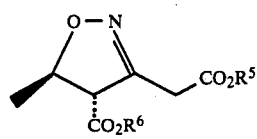

followed by reduction to yield:

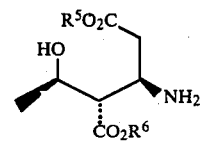

followed by cyclization and deblocking to yield:

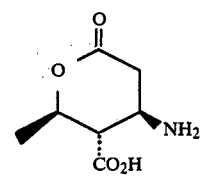

followed by alcoholysis with $R^1OH$ to form:

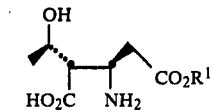

followed by cyclizing to form:

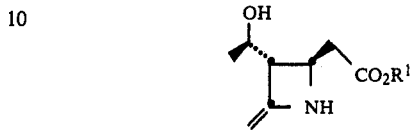

followed by carboxyl-deprotecting, activating and treating with $(R^3O_2CCH_2CO_2)_2Mg$ to form:

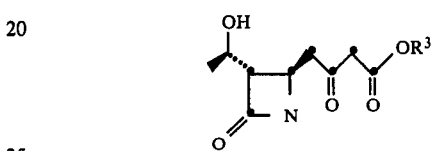

followed by deprotecting, diazotizing, and cyclizing to form:

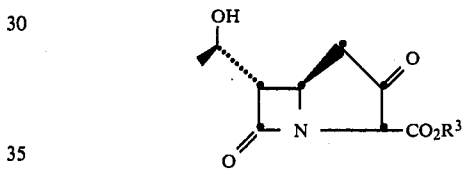

followed by activating, treating with $HSCH_2CH_2NHR^4$ and deprotecting wherein $R^1$, $R^3$, $R^4$, $R^5$ and $R^6$ are removable protecting groups.

* * * * *